(12) United States Patent
Pedersen (10) Patent No.: US 11,868,336 B2
(45) Date of Patent: Jan. 9, 2024

(54) DATA LOGGER FOR DENTAL OR MEDICAL AUTOCLAVE

(71) Applicant: Alpha Micro Tech Inc., Brantford (CA)

(72) Inventor: Frank Pedersen, Brantford (CA)

(73) Assignee: Alpha Micro Tech Inc., Brantford (CA)

(*) Notice: Subject to any disclaimer, the term of this patent is extended or adjusted under 35 U.S.C. 154(b) by 57 days.

(21) Appl. No.: 17/679,266

(22) Filed: Feb. 24, 2022

(65) Prior Publication Data

US 2022/0207015 A1 Jun. 30, 2022

Related U.S. Application Data

(62) Division of application No. 16/360,529, filed on Mar. 21, 2019, now Pat. No. 11,334,553.

(30) Foreign Application Priority Data

Mar. 22, 2018 (CA) .................................. CA 2998927

(51) Int. Cl.
G06K 7/14 (2006.01)
G06F 16/23 (2019.01)
A61L 2/07 (2006.01)
A61L 2/24 (2006.01)

(52) U.S. Cl.
CPC ............ *G06F 16/2358* (2019.01); *A61L 2/07* (2013.01); *A61L 2/24* (2013.01); *G06K 7/1413* (2013.01); *A61L 2202/14* (2013.01); *A61L 2202/24* (2013.01)

(58) Field of Classification Search
CPC ...... G06F 16/2358; A61L 2/07; G06K 7/1413
See application file for complete search history.

(56) References Cited

U.S. PATENT DOCUMENTS

| 2007/0094303 | A1* | 4/2007 | Zwingenberger .... G06Q 10/087 |
| 2015/0374868 | A1 | 12/2015 | Bruce |
| 2016/0265040 | A1 | 9/2016 | Baumgartner |
| 2018/0348061 | A1 | 12/2018 | D'Onofrio |

* cited by examiner

*Primary Examiner* — Kevin Joyner
(74) *Attorney, Agent, or Firm* — Laurence P. Colton; SMITH TEMPEL BLAHA LLC (57) ABSTRACT

A data logger for use with a dental or medical autoclave is disclosed. The data logger receives data transmitted from the autoclave and stores the data on secure digital memory. The data logger assigns a cycle number to data received associated with a particular sterilization cycle and stores the data associated with this cycle number on the memory until the associated sterilization cycle is complete at which time a new cycle number is assigned to the incoming data associated with a new sterilization cycle. A visual display is provided that displays the data associated with the various stages of a sterilization cycle of the autoclave in real-time for quick reference and verification. The data logger provides for compact and convenient data storage of dental sterilization cycles for record keeping and verification purposes.

3 Claims, 8 Drawing Sheets

DATA LOGGER FOR DENTAL OR MEDICAL AUTOCLAVE

CROSS REFERENCE TO RELATED APPLICATIONS

This patent application claims priority on and is a divisional of U.S. patent application Ser. No. 16/360,529 having a filing date of 21 Mar. 2019, which claims priority on and the benefit of Canadian Patent Application No. 2,998,927 having a filing date of 22 Mar. 2018.

BACKGROUND OF THE INVENTION

Technical Field

The present disclosure relates to a data logger for storing and displaying data related to the sterilization cycles of a dental or medical autoclave or sterilizer.

Prior Art

Dental and medical autoclaves for sterilizing dental or medical equipment and/or instruments are known. Autoclaves use pressurized steam at elevated temperatures through specifically timed cycles in order to sterilize reusable dental and/or medical equipment and instruments. In order to keep a record of the sterilization process, autoclaves are often connected to a printer that provides a real-time printed record of the information associated with each cycle of the various sterilization processes while the autoclave is in use. The printed record provides confirmation of the temperatures and pressures reached during the various cycles as well as the duration of the various cycles for reference and/or verification of the sterilization process. Having the printer run continuously while the autoclave is in use is cumbersome in that the printer requires a constant supply of paper with the printer continuously producing the printed record which must then be stored. Reviewing the printed record is also labour intensive since it is difficult to associate the printed record of sterilization and/or cycle data with the actual autoclave sterilization cycle for verification purposes. Cross contamination of sterilized instruments with paper records and other record keeping materials and equipment is also of concern. Accordingly, improved collection, storing and verification of data associated with the operation of dental and medical autoclaves is desirable.

BRIEF SUMMARY OF THE INVENTION

In accordance with an example embodiment of the present disclosure there is provided a data logger for use with a dental or medical autoclave, the data logger comprising an outer casing; a microprocessor disposed within the outer casing and coupled to an input for receiving sterilization data transmitted from the autoclave; a memory disposed within the outer casing operably coupled to the microprocessor for receiving and storing data transmitted from the autoclave to the microprocessor; and a visual display screen disposed on an outer surface of the outer casing and operably coupled to the microprocessor for displaying data received from the autoclave.

In another embodiment there is provided a data logger for use with a dental or medical autoclave, the data logger comprising an outer casing; a microprocessor disposed within the outer casing and coupled to an input for receiving sterilization data transmitted from the autoclave; a memory disposed within the outer casing operably coupled to the microprocessor for receiving and storing data transmitted from the autoclave to the microprocessor; and a touchscreen in communication with the microprocessor by way of a wired or wireless connection, the touchscreen providing a means for displaying data received from the autoclave and for inputting data into the memory.

Also provided is a method of logging data from the operation of an autoclave, the data comprising the temperature, pressure and time of sterilization of a sterilization process carried out in the autoclave, the method comprising (i) with a bar code scanner, scanning a pre-printed bar code and storing identification data related to the bar code in a memory, (ii) associating the bar code with a specific instrument load to be sterilized together in the autoclave, (iii) operating the autoclave through a sterilization process to sterilize the instrument load, (iv) recording the date of the sterilization process and the temperature, pressure and time of the sterilization process in the memory and associating the recorded date, temperature, pressure and time of sterilization with the scanned bar code.

BRIEF DESCRIPTION OF THE DRAWINGS

Reference will now be made, by way of example, to the accompanying drawings which show example embodiments of the present application, and in which.

Similar reference numerals may have been used in different figures to denote similar components.

DETAILED DESCRIPTION OF PREFERRED EMBODIMENTS

Figure 7:
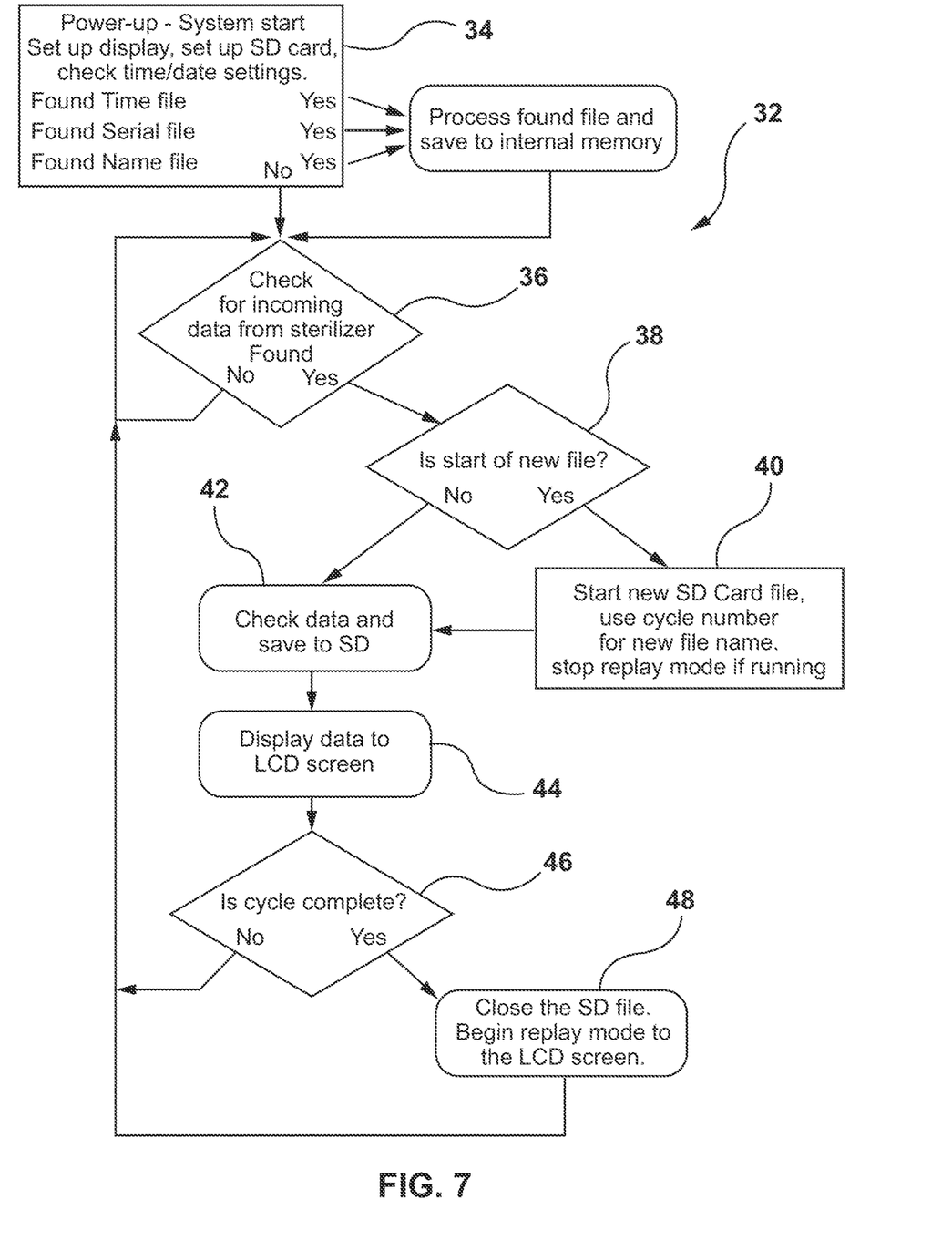
FIG. 7 is a flowchart detailing the operation of the data logger according to an example embodiment of the present disclosure.
Figure 8:
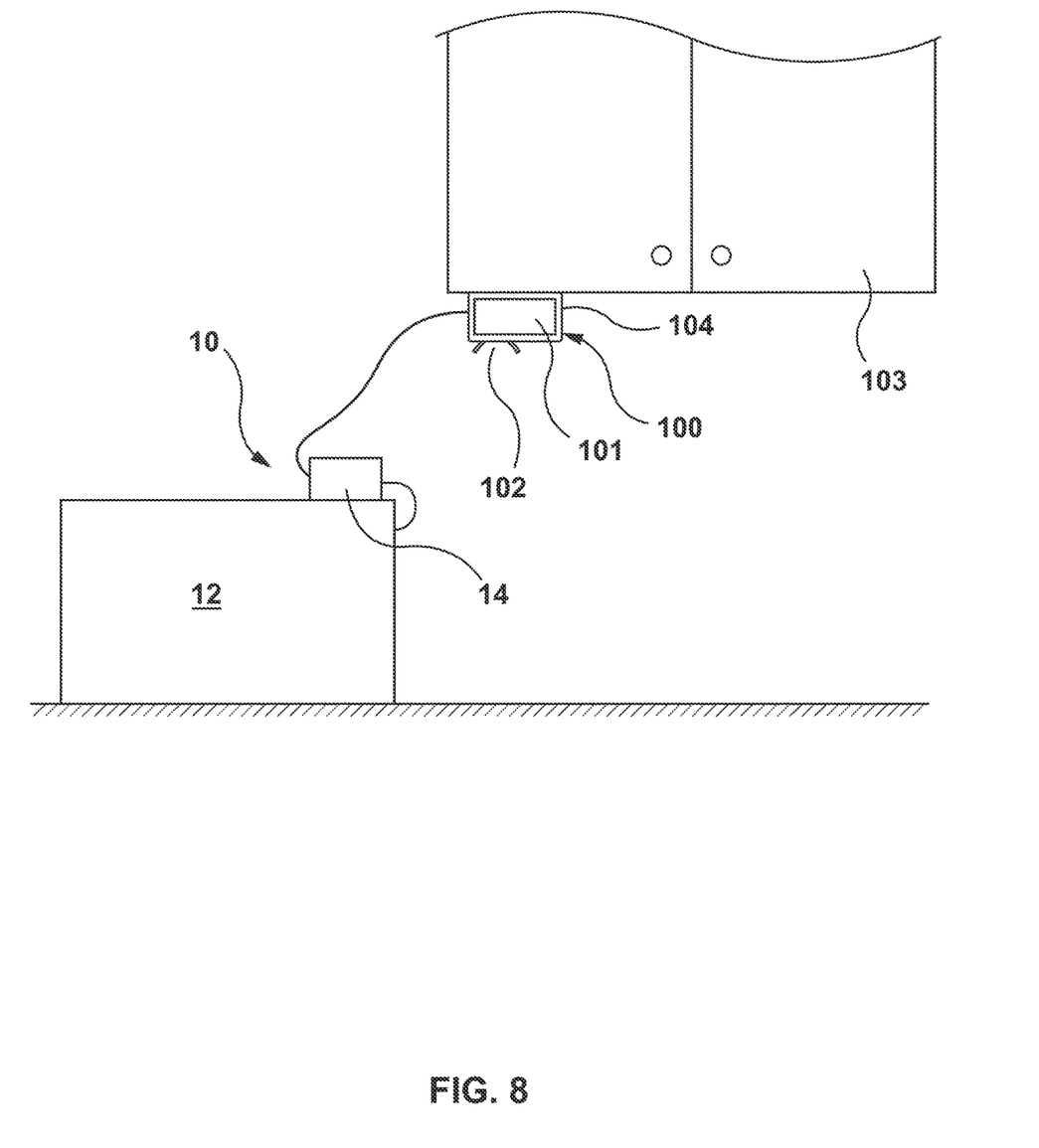
FIG. 8 is a schematic of an alternate embodiment of the data logger of the present invention in use with an autoclave.

Referring now to FIGS. 1-8, there is shown a data logger 10 according to an example embodiment of the present disclosure. The data logger 10 is designed to electronically record and display sterilization cycles from medical and dental sterilizers, is configured for use with a dental or medical autoclave 12, and is mounted externally to the autoclave 12 as shown in FIG. 8. The data logger 10 has an outer housing or casing 14 which houses the electrical components and internal subsystems of the data logger 10. In some embodiments, for example as shown in FIG. 1A, the casing 14 is a hard, two-part plastic structure comprising a base portion 14a and a top portion 14b disposed in mating relationship to form the housing 14 enclosing an open interior space. In some embodiments, for example, the top portion 14a and the base portion 14b are secured together by way of corresponding interlocking features disposed on the top portion 14a and the base portion 14b. In other embodiments, the top portion 14a and the base portion 14b may be secured together with separate fasteners of any suitable type.

The data logger 10 includes a data connector cable 16 that connects the data logger 10 to the corresponding dental or medical autoclave 12. A visual display screen 18 is disposed on a front surface of the data logger 10 for displaying data associated with the sterilization cycles of the autoclave 12. In some embodiments, for example, the visual display screen 18 is an LCD screen.

A microprocessor 20 that controls the overall operation of the data logger 10 may be disposed within the open interior space defined by the outer casing 14. The microprocessor 20 is mounted on a printed circuit board (PCB) 22 that is housed within the casing 14 and which is powered by a power source 24, for example a battery, or via an electrical cable or wire that connects to a power source external to the data logger 10. The data connector cable 16 connects to the printed circuit board 22 for transmitting data from the autoclave 12 to the microprocessor 20. Alternately, both the autoclave and the microprocessor may be fitted with wireless communication means (eg Bluetooth, etc) top permit a wireless transmission of data. The data transmitted to the microprocessor 20 from the autoclave 12 relates to information associated with the various sterilization cycles that occur during regular operation of the autoclave such as, for example, data relating to the temperature and/or pressure achieved during a particular cycle, the duration of each cycle or stage of cycle, etc.

The microprocessor 20 interacts with other subsystems of the data logger 10 such as a memory 26 which stores the data transmitted from the autoclave 12, and also interacts with the visual display screen 18 for displaying elements of the data received from the autoclave 12 at the appropriate time.

Figure 1:
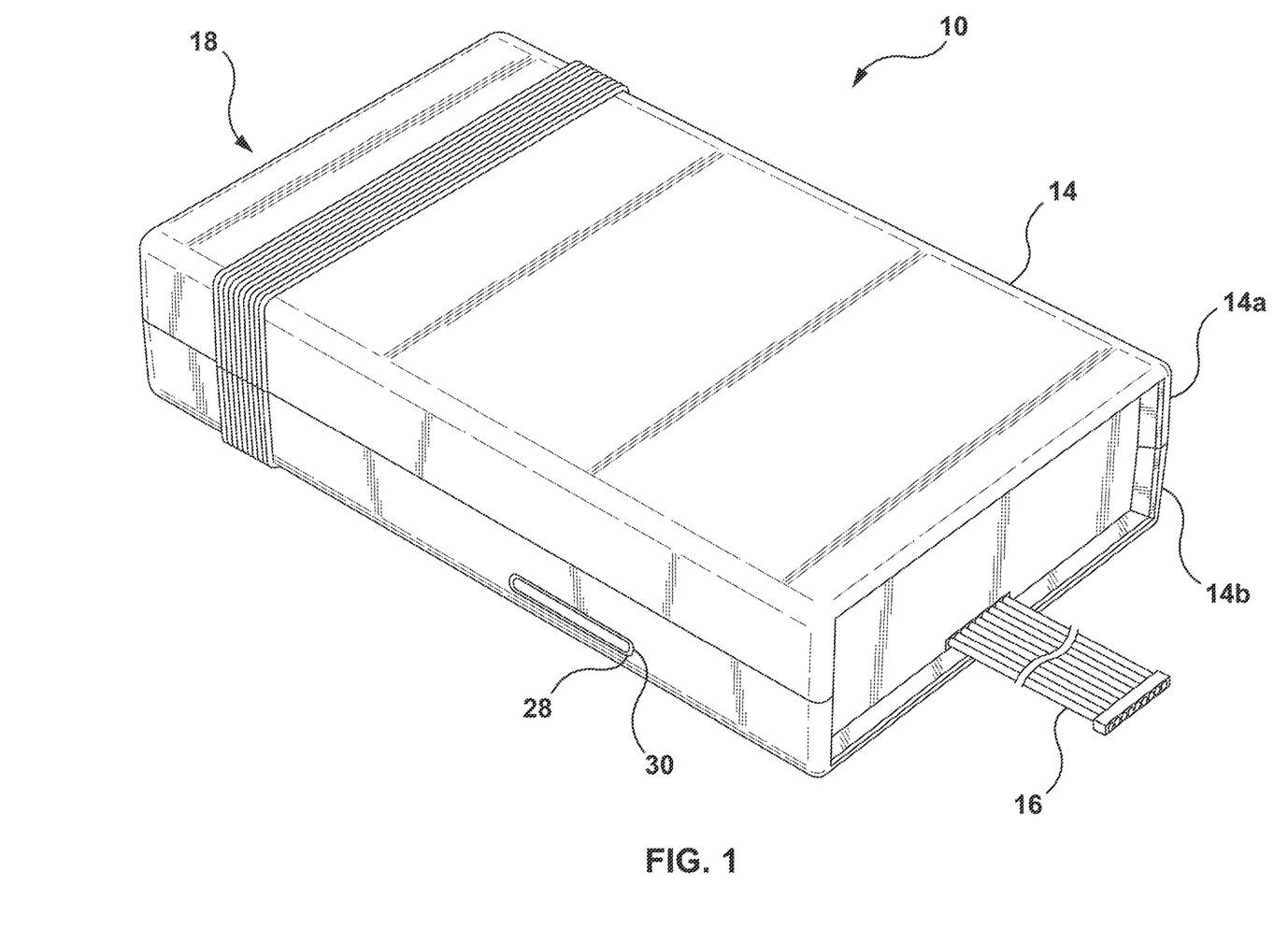
FIG. 1 is a rear top perspective view of a data logger according to an example embodiment of the present disclosure.
Figure 1A:
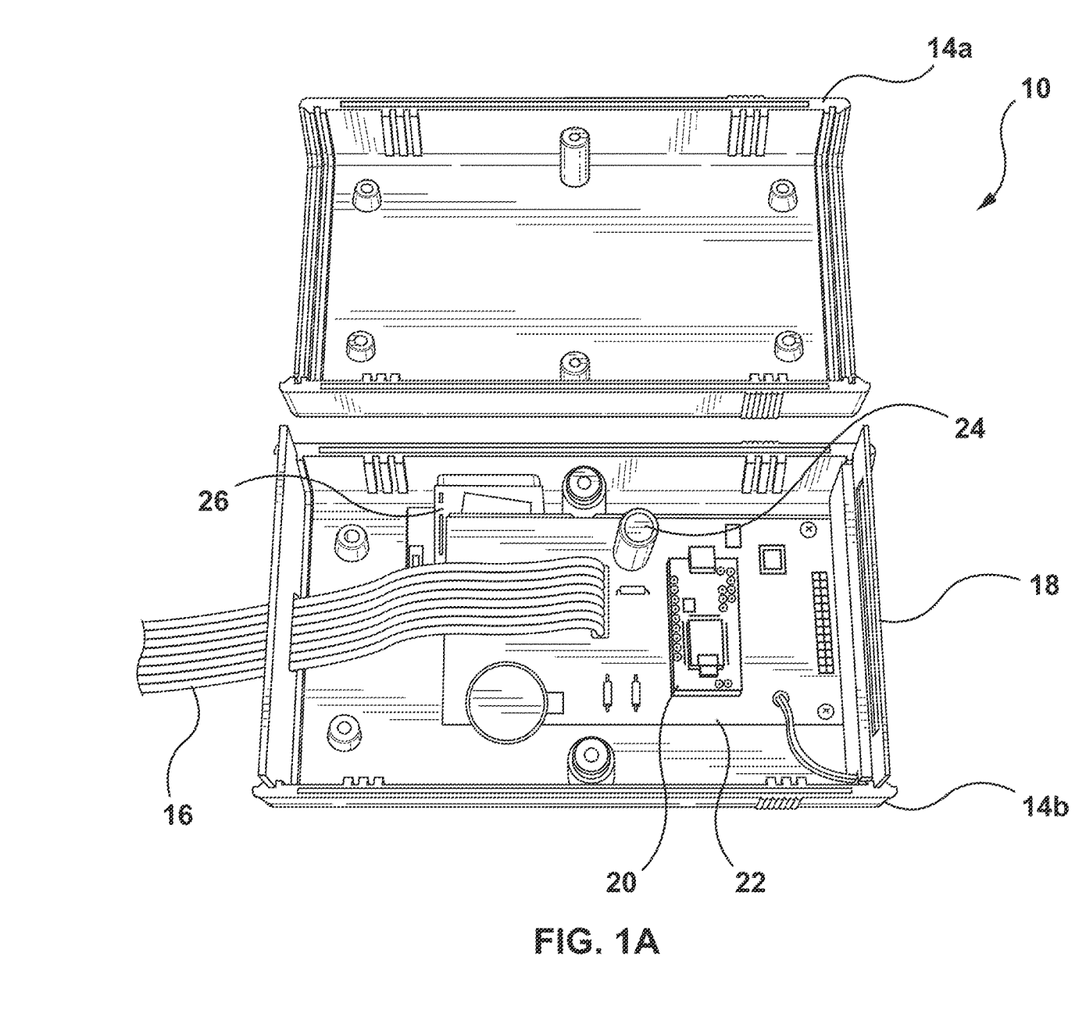
FIG. 1A is a top plan view of the data logger of FIG. 1 with the casing opened.
Figure 2:
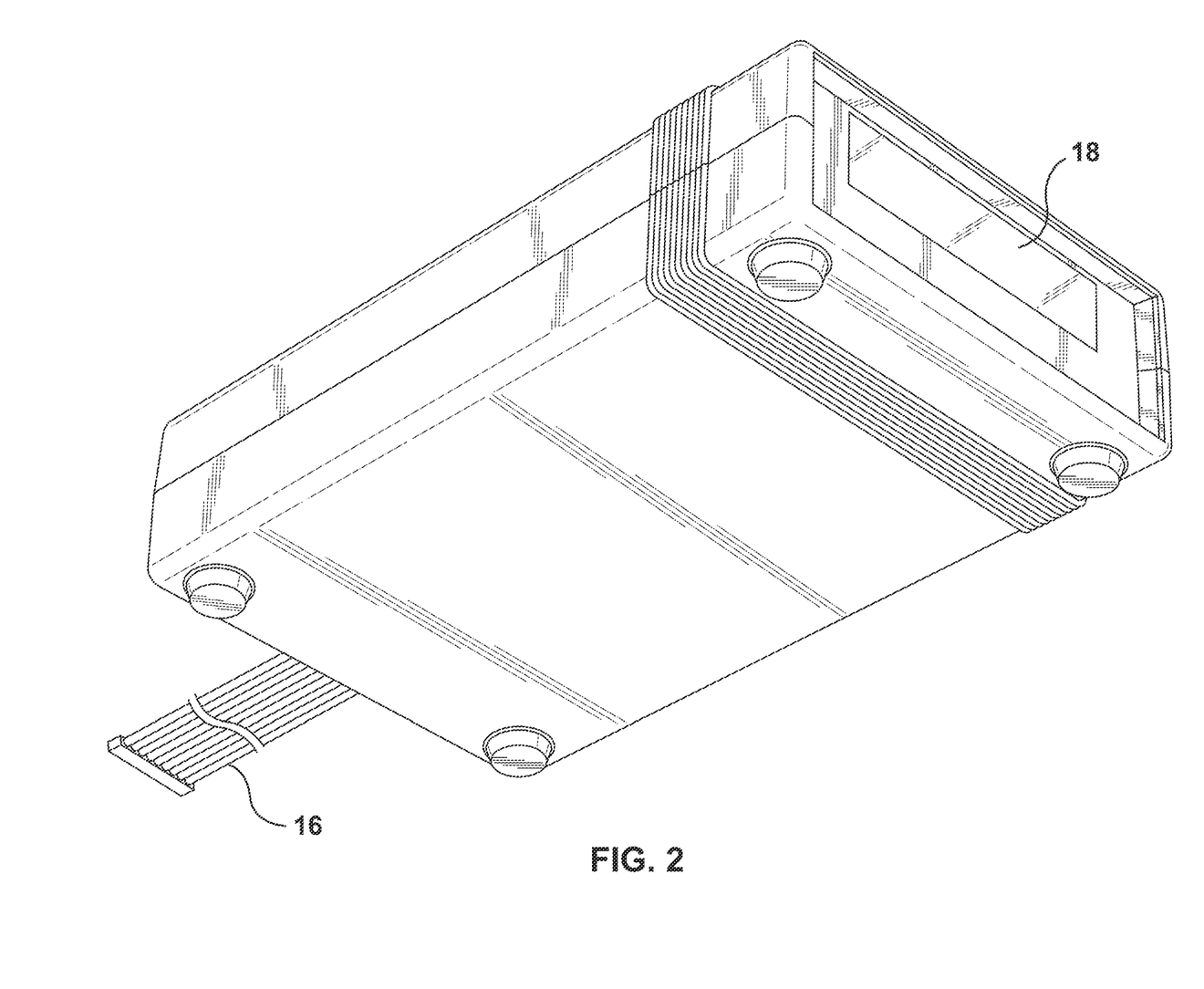
FIG. 2 is a front bottom perspective view of the data logger of FIG. 1.
Figure 3:
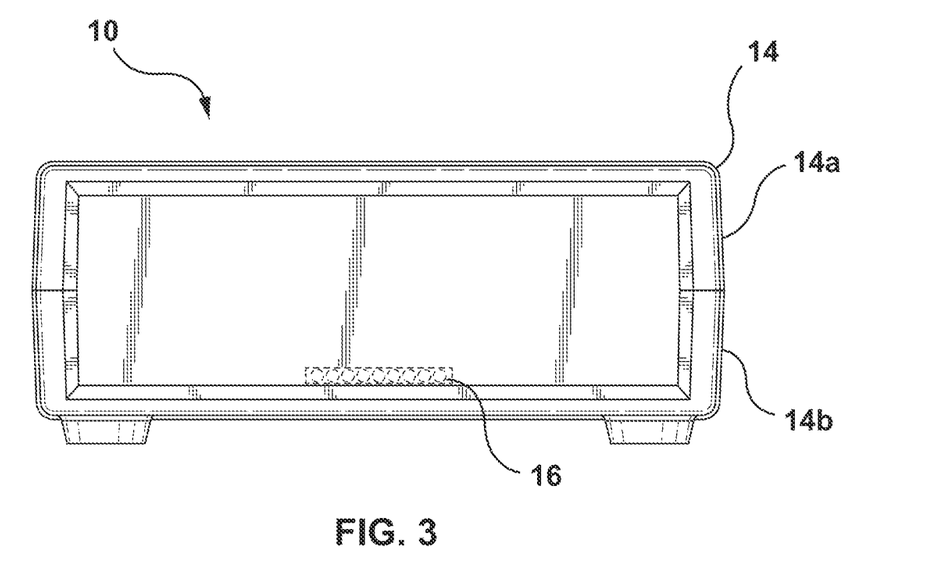
FIG. 3 is a rear elevational view of the data logger of FIG. 1.
Figure 4:
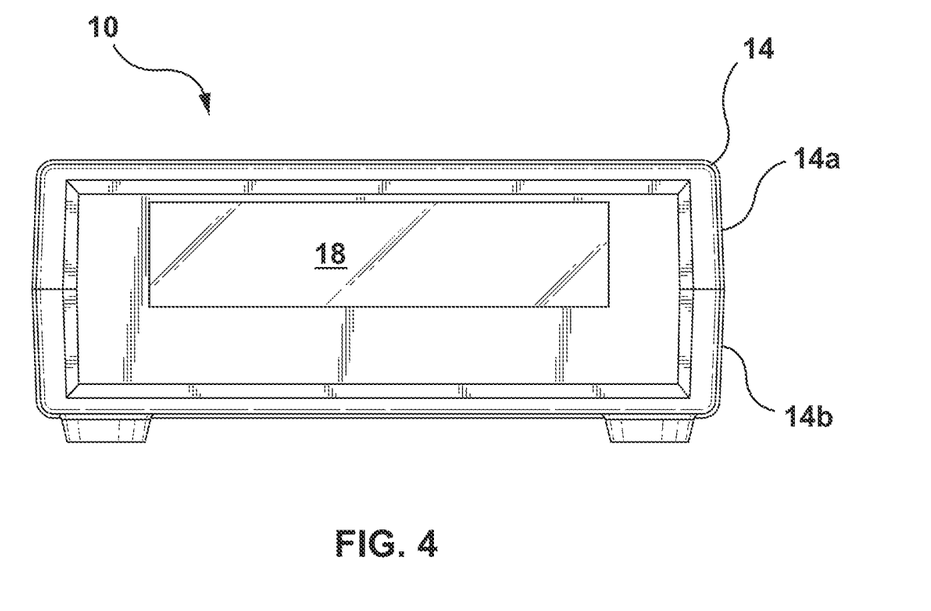
FIG. 4 is a front elevational view of the data logger of FIG. 1.
Figure 5:
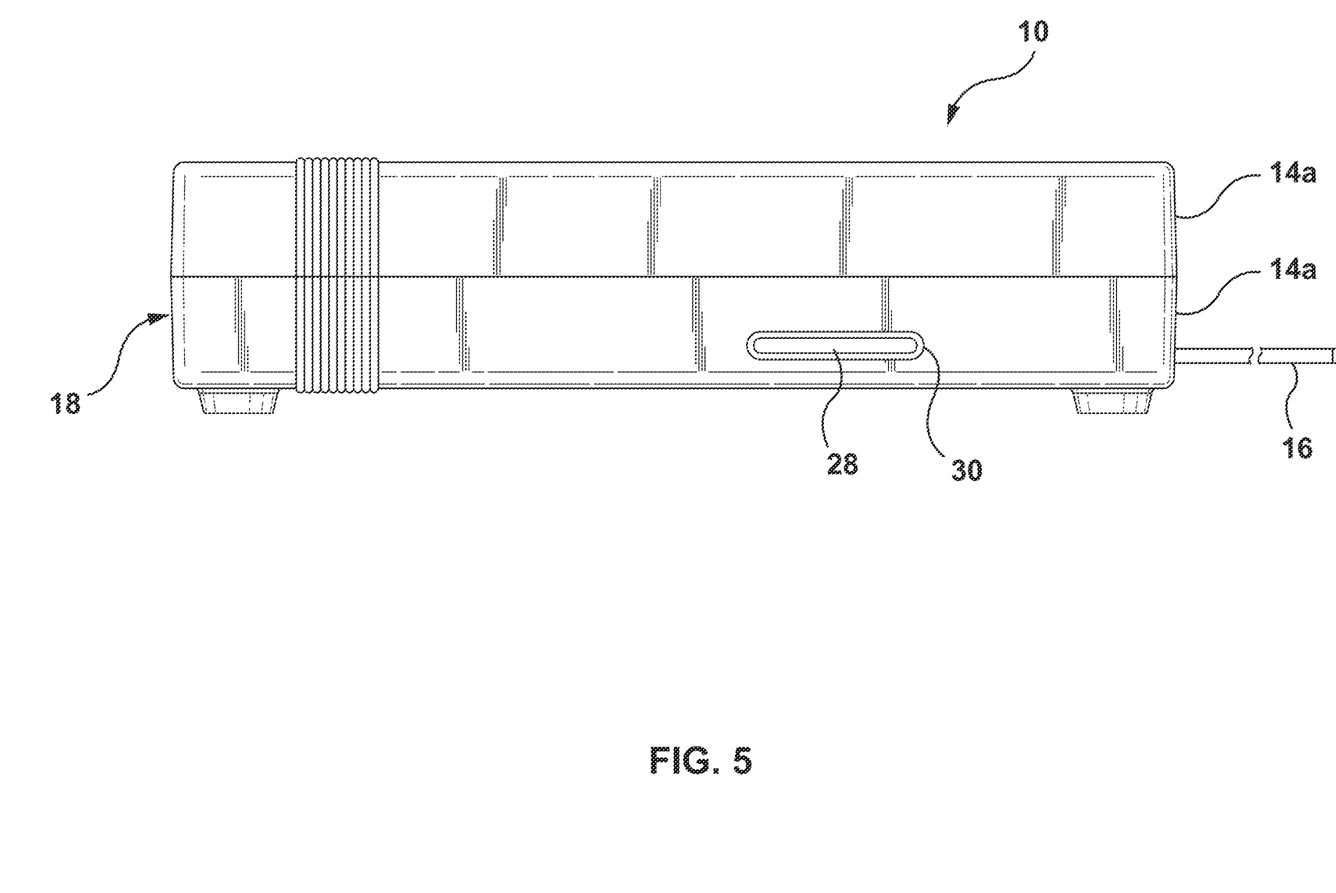
FIG. 5 is a right side plan view of the data logger of FIG. 1.
Figure 6:
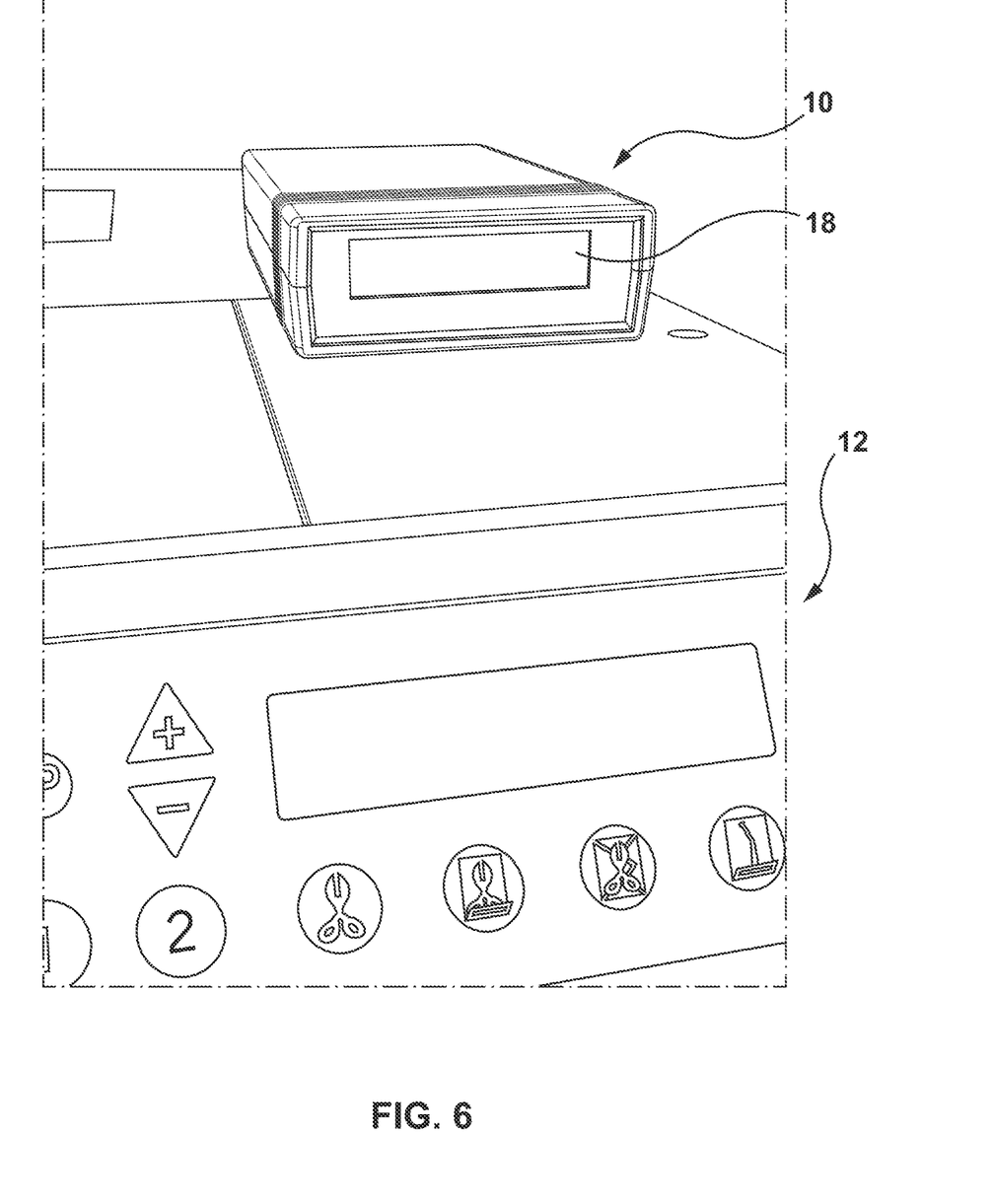
FIG. 6 is a front perspective view of the data logger installed for use with a dental or medical autoclave.

In some embodiments, the memory 26 is in the form of a secure digital (SD) memory card 28 that is removably mounted within a corresponding memory card-receiving slot or opening 30 disposed in the casing 12 as shown, for instance in FIGS. 1 and 5. The SD memory card 28 stores the data transmitted from the autoclave 12 and can be removed from the data logger 10 so that the data can be transferred to a different computer or a back-up storage device and re-inserted or replaced for use with the data logger 10, as needed. Other forms of memory devices are also contemplated and include hard drives, removable hard drives, USB sticks, etc. Removable memory in the form of an SD card etc. permits data to be transferred to a computer or other data storage device for long term storage. Alternately, the data logger may be wireless or wire connected to a computer network to permit the transfer and long term storage of data, as well as permitting data to be reviewed, analyzed and integrated into patient record keeping software or other business or practice management software.

Operating system software 32 is stored on and used by the microprocessor 20 or on a similar storage element working in conjunction with the microprocessor 20. The microprocessor 20 enables execution of the software applications for proper operation of the data logger 10. With reference now to FIG. 7, the operation of one embodiment of the operating system software 32 of the data logger 10 will now be described further detail.

At the beginning of a sterilization process by the autoclave 12, the data logger 10 powers-up and at initial set-up stage 34, the microprocessor 20 runs through preliminary software applications logging date and time settings and searching for a serial number and/or file name to begin the data logging process. If no file name or serial number is found at start-up of the data logger 10 during the initial set-up stage 34, the microprocessor 20 then operates to check for incoming data being transmitted from the corresponding autoclave 12 at step 36. If it is found that incoming data is being transmitted, the microprocessor 20 then operates to check whether the incoming data is the start of a new data file or if the incoming data is associated with an existing data file at step 38.

If at step 38 the incoming data is determined to be the start of a new data file, for instance the beginning of a new sterilization cycle, a cycle number is assigned and a new data file is created using the cycle number as the file name at step 40. Once a cycle number and file name have been assigned at step 40, the incoming data is received by the microprocessor 20 and is saved to the corresponding data file in the memory 26 and/or SD memory card 28 at step 42. As the data is being received and saved to the memory, the data is also simultaneously displayed on the visual display screen 18 at step 44. The receiving, saving and displaying of data continues until the microprocessor 20 operates via the operating software 32 to determine whether the cycle is complete at step 46.

If the cycle is determined to be complete at step 46, the data file stored by the memory and/or on the SD memory card 28 is closed and the microprocessor 20 operates to return the system to step 36 to check for incoming data from the autoclave 12. If no incoming data is detected, the system enters a holding pattern continuously checking for incoming data from the autoclave 12 until such time as incoming data is collected. During this holding pattern, the last reading of cycle data that was displayed on the visual display screen can remain visible along with the corresponding cycle number for ease of reference.

If, at step 46, it is determined that the cycle is not complete, the system continues to check for incoming data at step 36. If incoming data is detected and it is determined that the incoming data from the autoclave 12 is part of a current sterilization cycle that already has an assigned cycle number and file name at step 38, the system then operates to receive and save the incoming data to the memory 26 an/or SD memory card 28 to the same cycle number and file number created based on the cycle number and to update the visual display screen 18 to the current data related to the sterilization cycle associated with the same cycle number at steps 42 and 44. Accordingly, at any one time during the sterilization process, the specific cycle number and data associated with the specific stage of the sterilization process can be viewed on the visual display screen 18.

Once the visual display screen 18 has been updated to the most current data, the microprocessor 20 continues the cycle and determines whether the cycle is complete at step 46. If it is determined that the cycle is complete, the data file is closed at step 48 and automatically begins a re-play mode.

The re-play mode is triggered at the end of each recorded sterilization cycle and the parameters such as temperature, pressure and time, are replayed on the display screen in a continuous loop until the next cycle is selected or started. The loop replays back in an accelerated mode allowing all the parameters to be displayed in about 15-20 seconds. This feature allows the operator to visual verify that the sterilization parameters where completed successfully in accordance with the requirements of predetermined standards. This information is also recorded to the SD card under year and month folders.

The Practice/Doctor's name and sterilizer's serial number can be added and programmed into the internal memory. This information is then included in each record saved to the SD card allowing for a more detailed record of the sterilization cycle. This is also to ensure that the records came from that sterilizer.

In regard to security, every sterilization cycle file saved to the SD card has an electronic key added to the end of each saved record. This electronic key can be used to verify the integrity of the information contained in saved cycle files.

Once a new cycle is initiated, incoming data is detected at step 36, and a new cycle number increased by a factor of one based on the previously record file number and held in replay mode is assigned along with the new file name. The operating software application 32 continues to run for as long as the data logger 10 and the autoclave 12 are in use.

Since the operating system 30, 32 provides for a replay mode of the data collected during the previous sterilization cycle, the data logger 10 can assign the next appropriate cycle number and file name to the next set of incoming data for a new sterilization cycle, even if the data logger 10 has been turned-off for a period of time.

FIG. 8 shows an alternate embodiment of the invention. Here, data logger 10 may include an input device 100 that can be comprised of a touchscreen. The touchscreen may have associated with it a keyboard, a voice activation means, mouse, or other input device. In the particular embodiment shown, input device 100 is in the form of a touchscreen display unit 101. In addition, in the embodiment shown touch screen 101 is positioned remote from housing 14 and at a location that may be more convenient for accessing and use by an operator. Touchscreen 101 may be connected to microprocessor through hard wiring or through various wireless means. However, in alternate embodiments, touchscreen 101 could be incorporated into housing 14. In a further alternate embodiment, both housing 14 and touchscreen 101 could be incorporated into the housing or casing of autoclave 12.

In this embodiment touchscreen 101 serves the dual purpose of displaying information from data logger 10 and also acting as a means through which information and data can be input and stored into memory. For example, when the autoclave has concluded a sterilization cycle the operator will be prompted by visual indicators on the touchscreen to verify that the critical parameters have been met (typically that a minimum temperature and pressure have been reached for a minimum required length of time), following which the operator can input his or her name or other identifier into the touchscreen so that the individual verifying the sterilization cycle can be tracked. In that manner, the date and time of the sterilization cycle, the sterilization parameters, the fact that the sterilization has been verified, and an indication of the individual who conducted the verification, can all be stored together for later access if necessary.

In some instances local requirements or practices require that sterilization indicators accompany instruments that are loaded into an autoclave. Commonly such indicators change colour or are otherwise modified to provide a visual confirmation that sterilization parameters have been met or exceeded. In such instances, the operator may be prompted to also verify the condition of any such indicator as a further or secondary check to ensure that the sterilization parameters have been met.

In a further embodiment of the invention, data logger 10 may include a barcode scanner 102 as well as, in some instances, a barcode printer (not shown). Barcode scanner 102 communicates with microprocessor 20 through a wired or a wireless connection. Prior to the commencement of a sterilization process, an operator can load into the input device (through whatever means are available depending on the nature of the input device) details regarding the nature of the items to be sterilized (e.g., hygiene, restorative, endo, mixed load, etc). A pre-printed barcode can then be scanned by scanner 102 in order to input details regarding the sterilizer load into memory. The tray, pouch or cassette within which the items for sterilization are being retained can then be inserted, along with the bar code, into the autoclave and the sterilization process commended. Once sterilization has been completed, the operator will be prompted to "verify" the sterilization as generally indicated above. The sterilization parameters and the verification will be stored in memory and associated with the pre-scanned barcode. When accessed at a later date, the barcode associated with a particular set of sterilized instruments can be re-scanned, revealing to the user at the time an indication of when the instruments were sterilized, a verification that the sterilization parameters were achieved, and an indication of the individual who conducted the verification. In this manner the "shelf life" of sterilized instruments can easily be monitored to ensure that instruments that have been sterilized on a date too distant in the past with respect to regulatory requirements will be easily identifiable. The scanning of such a barcode will also act as a further verification that the individual accessing particular sterilized instruments verified the date and parameters of the sterilization before the instruments came into contact with a patient. Once again, as in the case of the critical autoclave parameters associated with the sterilization cycle, such data can be stored in the same file as the sterilization parameters for access at a later date if necessary.

It is contemplated that the barcode scanner may be in the form of any commonly used scanning devices including handheld and fixed devices. In one embodiment touchscreen 101 could be located within its own dedicated housing 104 that permits it to be mounted to the bottom of a wall cabinet 103 or similar structure. In that embodiment, barcode scanner 102 could be incorporated into the housing 104, thereby permitting an operator to easily and quickly pass a barcode beneath touchscreen 101 for scanning purposes.

From a thorough understanding of the above invention, it will be appreciated that the described device provides a mechanism by which all pertinent information concerning the sterilization of dental and/or medical instruments can be recorded for safekeeping and accessing at a later time. If desired, the described invention can be connected (either wirelessly or by wires) to an office network making all recorded data available on the network, and also permitting recorded data to be downloaded into patient files in patient management software systems. The described data logger also presents a fast and easy mechanism for validation of sterilization parameters in a way that is designed to simplify workflow in the sterilization area of an office, while helping to eliminate the need to record data using traditional pens and paper, which present potential avenues of contamination and cross contamination.

While a specific embodiment of a data logger for use with a dental/medical autoclave has been described, it will be understood that certain adaptations and modifications of the described embodiments can be made. Therefore, the above discussed embodiments are considered to be illustrative and not restrictive.

What is claimed is:

1. A method of logging data from the operation of an autoclave, the data comprising the temperature, pressure and time of sterilization of a sterilization process carried out in the autoclave, the method comprising:
- with a bar code scanner, scanning a pre-printed bar code and storing identification data related to the bar code in a memory,
- associating the bar code with a specific instrument load to be sterilized together in the autoclave,
- operating the autoclave through a sterilization process to sterilize the instrument load,
- recording the date of the sterilization process and the temperature, pressure and time of the sterilization process in the memory and associating the recorded date, temperature, pressure and time of sterilization with the scanned bar code,
- verifying that the temperature, pressure and time of the sterilization of the sterilization process meets pre-determined requirements, and
- inputting and storing a verification confirmation into the memory, the verification confirmation being associated with the scanned bar code.

2. The method as claimed in claim 1, including subjecting the pre-printed bar code to the sterilization process with the instrument load.

3. The method as claimed in claim 1, including subsequently re-scanning the pre-printed bar code to access the verification data and date of the sterilization process.

* * * * *